United States Patent [19]
Heimansohn

[11] 3,958,334
[45] May 25, 1976

[54] RESILIENT ARTIFICIAL DENTURE TOOTH

[75] Inventor: Henry C. Heimansohn, Danville, Ind.

[73] Assignee: Indiana University Foundation, Bloomington, Ind.

[22] Filed: Dec. 13, 1974

[21] Appl. No.: 532,513

[52] U.S. Cl. ............................................. 32/2; 32/8
[51] Int. Cl.² .......................................... A61C 13/00
[58] Field of Search ................................. 32/2, 8, 12

[56] References Cited
UNITED STATES PATENTS

| | | | |
|---|---|---|---|
| 1,105,476 | 7/1914 | Withycombe | 32/2 X |
| 1,223,450 | 4/1917 | Van Allen | 32/2 |
| 2,380,468 | 7/1945 | Saffir | 264/19 X |
| 2,577,769 | 12/1951 | Kane | 32/2 |
| 2,585,858 | 2/1952 | Schwartz | 32/10 R |
| 2,799,932 | 7/1957 | Lester et al. | 32/2 |
| 2,854,746 | 10/1958 | Lester et al. | 32/2 |
| 3,343,262 | 9/1967 | Burg | 32/2 |
| 3,413,721 | 12/1968 | Pickering | 32/2 |
| 3,826,002 | 7/1974 | Faust et al. | 32/2 |

FOREIGN PATENTS OR APPLICATIONS

| | | | |
|---|---|---|---|
| 2,102,564 | 4/1972 | Germany | 32/2 |

Primary Examiner—Louis G. Mancene
Assistant Examiner—Jack Q. Lever
Attorney, Agent, or Firm—Jenkins, Hanley & Coffey

[57] ABSTRACT

An artificial tooth for use in a denture comprising a base portion, an occlusal portion, and an intermediate portion sandwiched between and secured to the base portion and occlusal portion, the intermediate portion being resilient to permit the occlusal portion yieldably to move relative to the base portion. The intermediate portion is disposed generally at equal vertical distances from the occlusal surface of the occlusal portion and the ridge lap surface of the base portion. An anchor wire or wires or other connecting members are provided for limiting the movement of the occlusal portion relative to the base portion. Such an anchor wire may preferably be rigidly connected to the occlusal portion and loosely pivotally connected to the base portion with the anchor wire extending downwardly through the sandwiched intermediate portion. The loose pivotal connection permits the occlusal portion to move from its normal position toward the base portion even by tipping movement. Two such anchor wires prevent the occlusal portion from twisting relative to the base portion. The anchor wire or wires prevents the occlusal portion from moving from its normal position away from the base portion.

8 Claims, 9 Drawing Figures

RESILIENT ARTIFICIAL DENTURE TOOTH

The present invention relates to dentures and particularly to the provision of a resilient artificial tooth for use in dentures.

Artificial denture teeth have been about the same for approximately 170 years. Dentures have consisted of hard substances, shaped like teeth, permanently fastened to denture bases. Real human teeth represent individual units with roots in the jawbone and possessing slight individual vertical movement upon mastication. Human teeth are much more stable than dentures because they are individually anchored in the jawbone.

The lower denture causes the greatest problem because of the tongue tending to dislodge it during mastication and speech and also because the lower denture is horseshoe in shape as compared to the upper denture which has greater stability because it covers the entire roof of the mouth. It is estimated that an individual can bite with only one-sixth or less force with artificial dentures than with human teeth. Dentures are usually constructed for individuals in older age groups and such older peopele have poor eating habits with a poor diet. In addition, because of their ages, their alveolar ridges or gums which support the dentures are more sensitive to pressure, more easily irritated and inflamed and, usually, the alveolar ridges are resorbed to provide less area for the denture base to seat thereby compounding the problem. Also, the saliva of older people is less, providing less adhesion.

Consider an older individual getting dentures for the first time. He or she attempts to bite a food bolus or morsel on the right side, for example. As the individual closes on the bolus, the left side of the lower dentures will lift up from leverage on the right side to touch the upper dentures. As the closure is completed, the left side of the lower denture will return to its original position. This type of movement tends to irritate the hypersensitive oral mucosa.

It will be appreciated that the human bite is not merely opening and closing like a gate hinge, but, in addition, when chewing, has a complicated lateral and protusive movement with the mandibular teeth moving on a spherical pattern having a radius of four inches with the center of the sphere being above the mandibular teeth. The movements are different for each individual and are regulated by muscles of mastication and the temporomandibular joints.

My present invention provides an artificial tooth for a denture, the occlusal portion of that tooth having resilient resisted movement relative to the base portion. In a set of dentures, including upper and lower dentures, I could provide eight resilient lower posterior teeth (four on each side) that would have vertical individual movements of occlusal (biting) surfaces concurrently with tipping of the occlusal surfaces.

The prior art has suggested several forms of resilient artificial teeth. Such patents as the following United States patents appear to be representative of the prior art: U.S. Pat. No. 1,105,476 issued July 28, 1914; U.S. Pat. No. 2,577,769 issued Dec. 11, 1951; U.S. Pat. No. 3,104,465 issued Sept. 24, 1963; U.S. Pat. No. 3,241,238 issued Mar. 22, 1966; U.S. Pat. No. 3,327,392 issued June 27, 1967; U.S. Pat. No. 3,423,831 issued Jan. 28, 1969; U.S. Pat. No. 3,517,443 issued June 30, 1970; U.S. Pat. No. 3,827,145 issued Aug. 6, 1974; and U.S. Pat. No. 3,826,002 issued July 30, 1974.

I submit that the prior art of which I am aware does not disclose nor suggest an acceptable resilient artificial tooth for use in dentures for the reasons I shall outline hereinafter.

My preferred artificial tooth comprises a base portion, an occlusal portion, and an intermediate portion sandwiched between and secured to the base portion and occlusal portion, the intermediate portion being resilient to permit the occlusal portion yieldably to move relative to the base portion. The occlusal portion provides, at its upper end, an occlusal surface and the base portion provides, at its lower end, a ridge lap surface. Preferably, the intermediate portion is disposed generally at equal vertical distances from the occlusal surface and the ridge lap surface. The terms "generally at equal vertical distances" is intended to encompass a considerable latitude. Particularly, I prefer that the intermediate resilient portion be about one-half way up the height of the tooth, well below the occlusal surface and well above the ridge lap surface. The intermediate portion may have different thicknesses such as 1 mm, 1.5 mm, 2 mm, 2.5 mm, etc., up to, for instance, 4 or 5 mm if a patient has very resorbed ridges. A patient with excellent ridges would need thinner intermediate portions and a patient with resorbed ridges would need thicker intermediate portions.

I prefer that the base portion and the occlusal portion provide, respectively, upper and lower generally horizontally extending bonding surfaces and that the intermediate portion provide generally horizontally extending upper and lower surfaces bonded respectively to the lower and upper bonding surfaces of the occlusal and base portions. I prefer that these surfaces be generally congruently superposed such that the intermediate portion appears as a vertically narrow strip extending horizontally about the outer surface of the tooth.

By having the intermediate portion generally at the vertical center of the tooth, I can grind on the occlusal end or occlusal surface as well as upon the ridge lap end or ridge lap surface in order to fit the tooth in a particular denture. That is, it is my intention to have such resilient teeth provided to the dentists from the factory with different types of teeth and with intermediate portions of different thicknesses so that each dentist can select the particular tooth shape and compressibility. The tooth can be further modified by grinding upon its occlusal or rige lap ends without, in any way, changing the characteristics of the intermediate portion or the resilient portion.

The vertically narrow strip of resilient material extending about the vertical center of the tooth is very sanitary and easy to keep clean with the bulk of the resilient material being protected by the occlusal portion and base portion of the tooth.

By placing the intermediate region at generally the vertical center of the tooth, I provide for an optimal resiliently resisted movement of the occlusal portion. The horizontally extending resilient intermediate section of each lower posterior tooth reduces very significantly the rocking of the base portion of the denture on either side, right or left. The occlusal poriton will compress toward the base portion or against the resilient intermediate portion or tip in all directions such as mesial, distal, buccal, lingual or between these positions as dictated by the occlusion of the opposing dental arch. Thus, each tooth will automatically respond to changes in occlusion of the opposite dental arch. This results in balanced occlusion, less alveolar bone loss and greater comfort. I presently believe that the thickness of the resilient intermediate portion should be a minimum of 1 mm while the maximum thickness may range up to, for instance, 4 or 5 mm.

The compressive-resilient tooth of my invention allows individual teeth automatically to adjust in vertical and tipping movements to the patient's jaw movements and condyle inclination in occlusion, thus decreasing the need for extensive preconstruction registrations which are conventionally used in constructing dentures with conventional artificial teeth.

With my resilient teeth used as the posterior teeth of both sides for the lower denture, if a bolus of food is placed on the right working side, for example, between compressive resilient teeth and the teeth made to occlude, then the teeth on the right side will be depressed and the balancing side or left side will remain in conatact. Thus, the denture will be balanced continuously in mastication.

Further, in accordance with my invention, means is provided for connecting the occlusal portion to the base portion, the connecting means limiting the movement of the occlusal portion relative to the base portion. The connecting means may include an anchor wire connected between the occlusal portion and the base portion, and the anchor wire may be rigidly connected to the occlusal portion and pivotally loosely connected to the base portion. The anchor wire preferably extends through the intermediate portion such that it is entirely contained within the tooth.

I prefer to use an anchor wire which is generally U-shaped with the base of the wire rigidly secured to the occlusal porition to provide a pair of vertically extending legs, the distal ends of which are loosely pivotally secured to the base portion. Alternatively, I may use two such anchor wires, one end of each anchor wire being rigidly secured to the occlusal portion with the opposite end loosely pivotally secured to the base portion. I prefer to have the two legs of the U-shaped anchor wire or the two separate anchor wires spaced apart in the mesial-distal direction inasmuch as the tooth is longer in that direction than in the buccal-lingual direction. By having the two separate anchor wires or the two separate legs of the U-shaped anchor wire, I prevent rotation of the occlusal portion relative to the base, which rotation would result in dislodging of the occlusal portion.

My anchor wire retention system is importantly internal to the tooth and not exposed to the mouth.

Further, importantly, my connecting means or anchor wire means serve to prevent the occlusal portion from moving from its normal unloaded position away from the base portion to the extent that the resilient intermediate portion would be broken. My connecting means or anchor wire means permit the occlusal portion to move from its normal unloaded position toward the base portion to compress the resilient material of the intermediate portion.

Another problem not contemplated by the prior art resilient artificial teeth of the type which are constructed from resilient material or the upper or lower ends of which are constructed from resilient material has to do with the use of the split metal flask by a dentist to construct dentures. In such a flask, the teeth embedded in plaster are in one half and the model of the gum ridge is placed in the other half. Plastic is mixed like putty and placed between the two halves and the flask is squeezed together. If some of the teeth are resilient, then they will be compressed. After the denture is processed and removed from the flask and pressure removed, such compressed teeth will project over the other teeth making an incorrect occlusal plane. I have solved this problem by having lip projections on the buccal (cheek) side and lingual (tongue) side of the base portion of the tooth made from the same material as the tooth. Then, when the denture is mounted in the flask and compressed, these projections will touch the plaster and prevent improper compression during processing. After removal from the flask, these lip projections or lugs are easily ground off since the denture is normally polished anyway.

Other objects and features of my present invention will become apparent as this description progresses.

To the accomplishment of the above and related objects, my invention may be embodied in the forms illustrated in the accompanying drawings, attention being called to the fact, however, that the drawings are illustrative only, and that change may be made in the specific constructions illustrated and described, so long as the scope of the appended claims is not violated.

Figure 1:
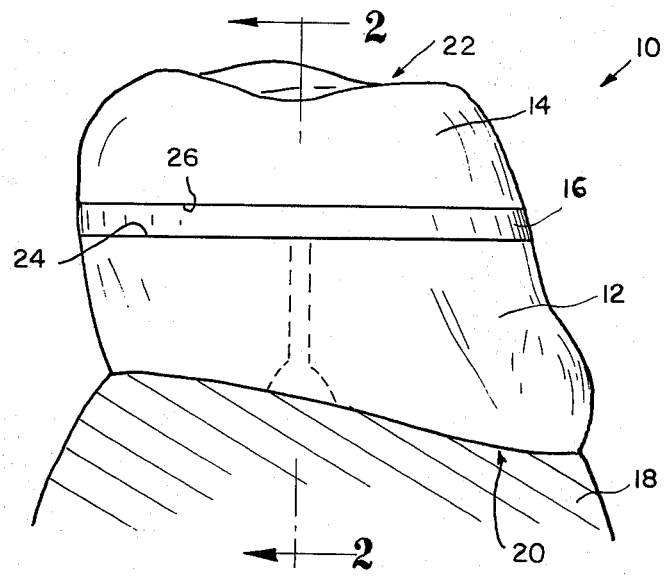
FIG. 1 is a fragmentary view of a portion of a denture showning my resiliently compressible tooth mounted thereon.
Figure 2:
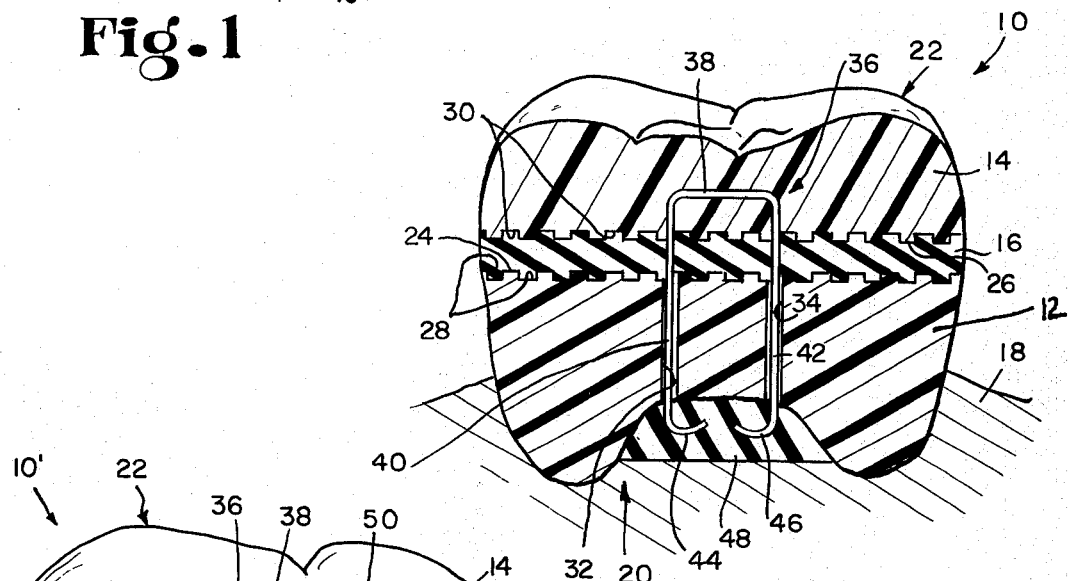
FIG. 2 is a fragmentary sectional view taken generally along the line 2—2 in FIG. 1.

Referring now to the drawings, and particularly to FIGS. 1 and 2, it will be seen that I have illustrated my artificial tooth 10 as comprising a base portion 12, an occlusal portion 14, and an intermediate resilient portion 16. The base portion 12 is mounted upon a denture base, a portion of which is indicated at 18. The reference numeral 20 indicates the ridge lap surface of the tooth while the reference numeral 22 indicates the occlusal surface of the tooth.

The intermediate portion 16 is sandwiched between the upwardly facing surface 24 provided by the base 12 and the downwardly facing surface 26 or lower surface provided by the occlusal portion 14. These surfaces 24, 26, which are preferably generally congruently superposed, lie in horizontally extending planes as bonding surfaces. In some cases, as illustrated, the bonding surfaces may be provided with small cavities or cross ridges as desired, as indicated by the reference numerals 28, 30.

Two holes 32, 34 extend vertically through the base portion 12, the holes lying in a plane which is approximately the center mesial-distal section of the tooth. Means for connecting the occlusal portion 14 to the base portion 12 is indicated generally by the reference numeral 36, the illustrative means including a generally U-shaped anchor wire having a base 38 which is rigidly secured to the occlusal portion 14 and vertically downwardly extending legs 40, 42 received, respectively, in the through holes 32, 34. The distal end portions 44, 46 of the legs 40, 42 are bent inwardly or toward each other as illustrated to restrain the anchor wire from moving vertically upwardly relative to the base portion 12. It will be seen that the ridge lap surface 20 provides a well into which the portions 44, 46 extend, which well may be filled with resilient material indicated at 48 which serves to prevent the base 18 material from entering the well during the processing of the dentures. Since the holes 32, 34 are larger in diameter than the wire legs 40, 42, some tipping movement or lateral movement of the occlusal portion 14 relative to the base portion 12 is permitted. Of course, the legs 40, 42 and the end portions 44, 46 can move downwardly relative to the base portion 12 to accommodate the compression of the resilient portion 16.

Figure 3:
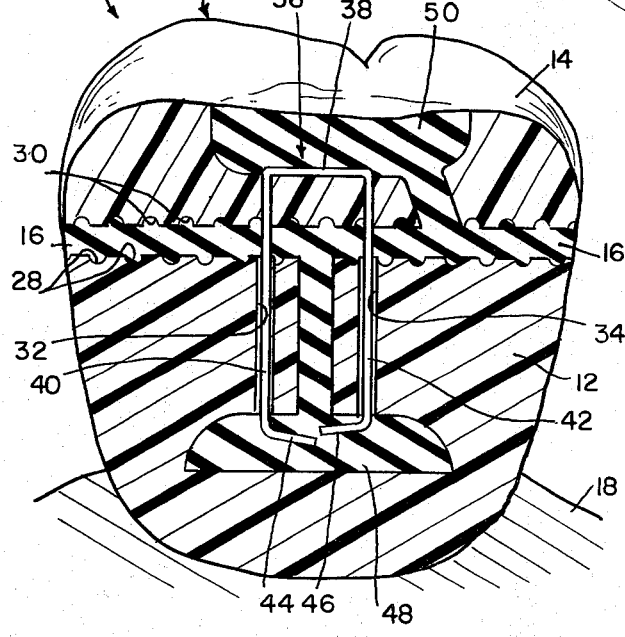
FIG. 3 is a fragmentary sectional view of another slightly different tooth in accordance with my present invention.

The embodiment of FIG. 3 indicated generally by the reference numeral 10', is very similar to the embodiment of FIGS. 1 and 2, like reference numerals representing like parts. The primary difference in the embodiment of FIG. 3 is the provision of a hollowed-out cavity 50 into which the resilient material is injected to cushion the upper or base portion 38. Thus, in the embodiment of FIG. 3, the anchor wire is not so rigidly attached to the occlusal portion 14.

I have said that the anchor wire 36 is rigidly secured to the occlusal portion 14 in FIGS. 1 and 2. This may be accomplished, for instance, by molding that occlusal portion with the wire extending into the mold. Any number of other techniques may be used rigidly to secure such an anchor wire or connector member to the occlusal portion.

Referring now to FIGS. 4–7, it will be seen that I have shown a resilient tooth indicated generally by the reference numeral 60, like reference numerals indicating like parts. One difference between the tooth 60 and the tooth 10 of FIGS. 1 and 2, is the manner in which the occlusal portion 14 is restrained from moving from its normal position away from the base portion 12. Instead of an inverted U-shaped anchor wire, there are two separate wires 40, 42 the upper ends of which are bent as indicated at 40a, 42a. Then, the distal ends of the through holes 32, 34 are enlarged as indicated at 32a, 34a to provide sockets 62, 64 in the base portion 12 for receiving the enlarged distal ends 66, 68 of the wires 40, 42. These enlarged openings 32a, 34a may preferably be plugged with a soft elastic material such as indicated at 70, 72 which prevents the hard acrylic base 18 material from flowing upwardly into the sockets 62, 64 to impede the movement of the enlarged distal ends 66, 68.

One advantage of my inventive resilient tooth is that a considerable amount of the occlusal surface 22 as well as the ridge lap surface 20 may be removed by grinding without, in any way, interfering with my mechanism for resiliently mounting the occlusal portion 14 on the base portion 12 and restraining the occlusal portion from moving away or tearing away from the base portion. The reference numerals 74, 76 indicate, respectively, the amount of occlusal surface 22 and ridge lap surface 20 which can be removed from the tooth 60. This feature applies also to the tooth 10, 10' of FIGS. 1, 2 and 3. Mass-produced teeth in accordance with my invention may be custom ground to fit a particular denture requirement.

Figure 4:
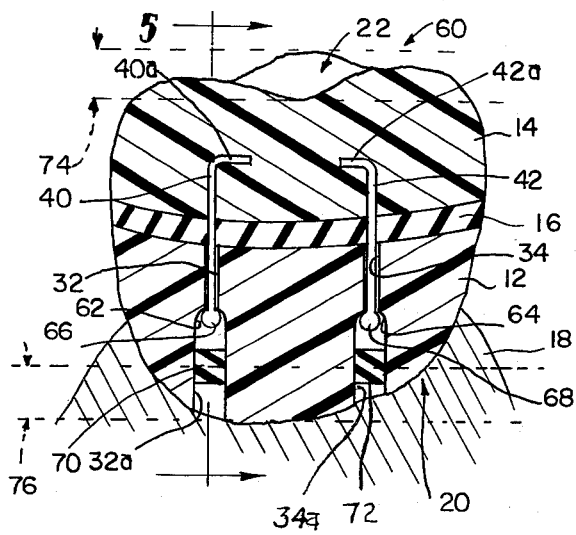
FIG. 4 is a fragmentary sectional view taken through the tooth along a vertical plane lying in the mesial-distal direction.

The sectional view of FIG. 4 is taken through a vertical plane extending centrally through the tooth in the mesial-distal direction. The two wires 40, 42 spaced apart in this plane serve to prevent the occlusal portion 14 from rotating about a vertical axis relative to the base portion 12, which rotation would be destructive to the intermediate resilient layer 16.

Figure 5:
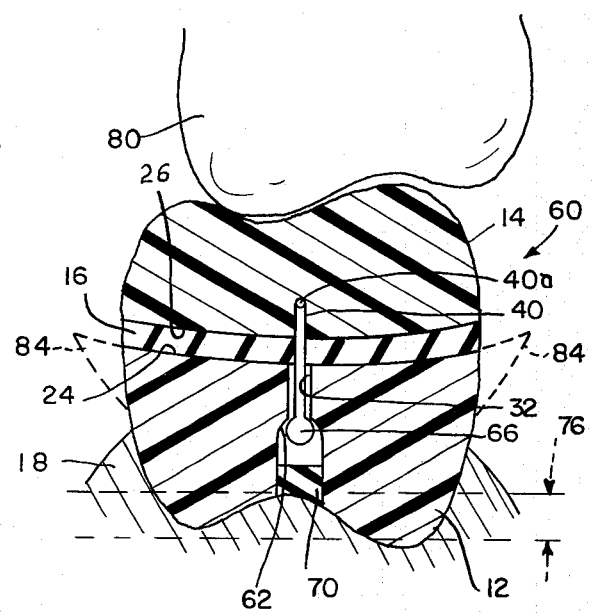
FIG. 5 is a fragmentary sectional view taken along the lines 5—5 in FIG. 4.
Figure 6:
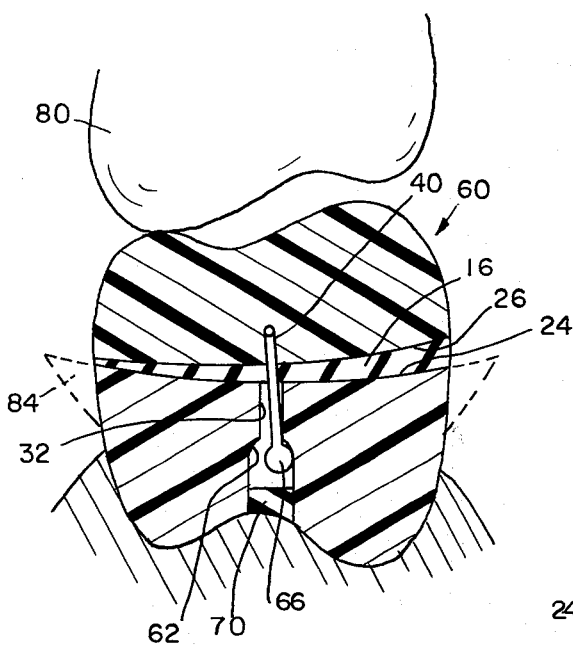
FIGS. 6 and 7 are sectional views similar to FIG. 5 but showing different tipping movement of the occlusal portion.
Figure 7:
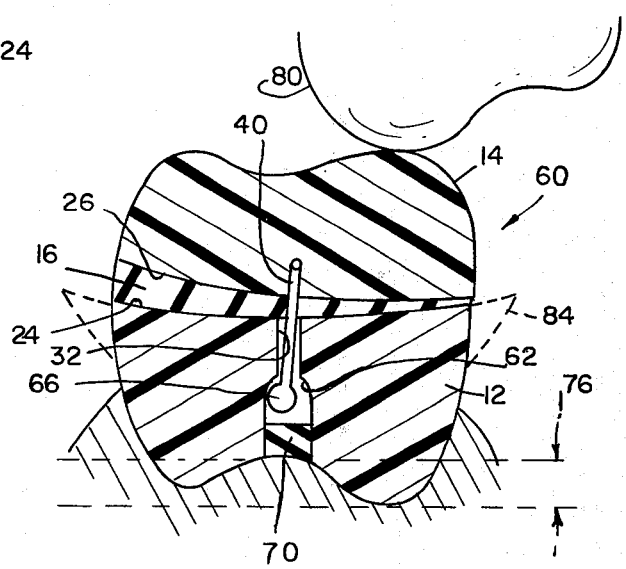

In the views 5, 6 and 7, I show an upper tooth 80 engaging the tooth 60, the views of FIGS. 5, 6 and 7 being taken in the buccal-lingual direction with the right-hand side of each view being the buccal or facial side and the left-hand side of each view being the lingual or tongue side. FIG. 5 shows the right side denture tooth 60 in occlusion with no pressure on the resilient portion 16. The retainer ball or enlarged end 66 is generally at the top of the socket 62. This position of the occlusal portion 14 represents its normal or unloaded position. It will be appreciated that the occlusal portion 14 cannot move vertically upwardly from the position of FIG. 5 because of the restraining feature of the enlarged end portion 66.

FIG. 6 shows a right lateral excursion of the mandible and lower denture with the occlusal portion 14 depressed and tipping to the lingual side. The retainer ball or enlarged end portion 66 depresses to the bottom of the socket 62 and is angulated in the over-sized hole 32. FIG. 7 shows a left lateral excursion of the mandible with the occlusal portion 14 depressed and tipping on the buccal side with the wire 40 angulated in the opposite direction relative to that shown in FIG. 6. The occlusal portion 14, therefore, can accommodate a considerable amount of excursion or grinding of the engaging occlusal surfaces of opposed teeth. The occlusal portion 14 can tip in any direction, i.e., from side to side in the buccal-lingual direction or from front to back in the mesial-distal direction.

Figure 8:
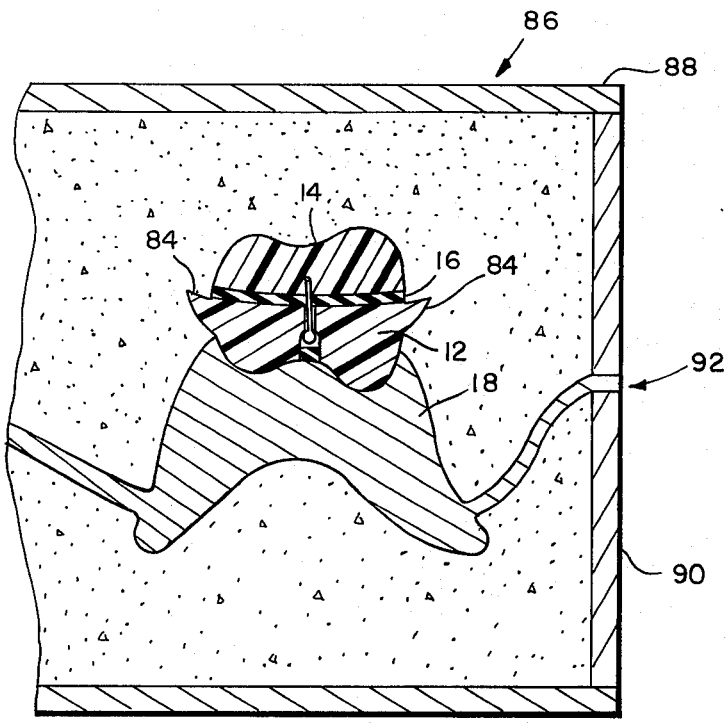
FIG. 8 is a fragmentary sectional view showing my tooth in a flask with lugs on the base portion of the tooth positioning the tooth in the dental plaster.

I show laterally outwardly extending lugs or lips 84 in dashed lines on the base portion 12 of the tooth 60. These lugs 84 serve to position the base portion 12 in the dental plaster or stone of a split metal flask indicated at 86 in FIG. 8, the flask having an upper half 88 and a lower half 90. The plastic material from which the denture base 18 is made is mixed like putty and placed between the two halves 88, 90 of the flask with the parting line of the flask being indicated at 92. Then the flask is squeezed together. The lugs 84 will position themselves in the dental plaster in the flask to keep the base portion 12 from being forced against the occlusal portion 14 to place the intermediate layer 16 in compression during the squeezing process. After the denture is removed from the flask, the lugs 84 are removed by grinding and polishing operations.

Figure 9:
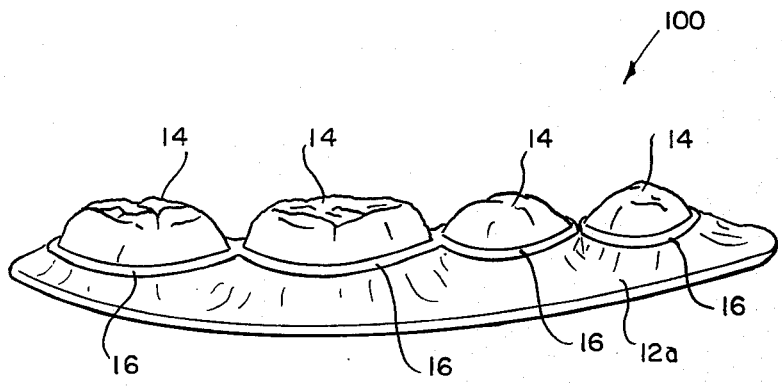
FIG. 9 is a perspective view showing a common base portion elongated in the mesial-distal direction with four occlusal portions resiliently mounted on the common base portion.

In the embodiment of FIG. 9, indicated generally at 100, four separate and individually yieldably movable occlusal portions 14 are mounted upon a common base portion 12a and resiliently supported thereon by intermediate portions 16. Each of the individual occlusal portions 14 in FIG. 9 are restrained from moving away from the base portion 12a by anchor wires such as indicated at 40, 42 in other embodiments. The entire base portion 12a, therefore, would be mounted upon a denture base 18 as an assembly.

I have shown the resilient teeth of my present invention on the lower posterior sides of dentures. It will be appreciated that my resilient teeth may be placed upon upper denture plates as well as lower plates and even on partial denture plates.

With the above description in mine, I now turn to the advantages of my resilient tooth.

The retention mechanism (anchor wires 40, 42) is completely enclosed within the tooth to prevent deterioration in the mouth, yet the mechanism allows the necessary compressive and tipping movement of the occlusal portion 14.

I can provide the correct degree of resilience by providing intermediate portions 16 having different thicknesses. Too much resilience would result in poor occlusion and rapid deterioration of the resilient portion and the patient would not be able to bite and chew properly.

Any type of occlusal manatomy may be used as the internal fixation, i.e., anchor wires and resilient portion 16, is the same. Common occlusion is like a mortar and pestle with the pestle part being the upper and convex portion of the upper tooth while the lower part is concave.

Of prime importance is the ability of the occlusal portion 14 to tip as well as be depressed or compressed. This prevents lateral stress on the denture base 18 and gums with consequent resorbtion of the gums.

I claim:

1. An artificial tooth comprising a rigid base portion providing a ridge lap surface, a rigid occlusal portion providing an occlusal surface, a resilient intermediate portion sandwiched between and secured to said base portion and occlusal portion, and means for connecting said occlusal portion to said base portion, said connecting means including a connecting member having one of its ends rigidly connected to said occlusal portion, and its opposite end pivotally and loosely connected to said base portion to permit controlled limited movement of said occlusal portion relative to said base portion, said connecting member extending through said resilient intermediate portion, said connecting member being a U-shaped anchor wire, the base of which is rigidly secured to said occlusal portion to provide a pair of vertically extending legs and the distal ends of which are loosely pivotally secured to said base portion.

2. An artificial tooth comprising a rigid base portion providing a ridge lap surface, a rigid occlusal portion providing an occlusal surface, a resilient intermediate portion sandwiched between and secured to said base portion and occlusal portion, and means for connecting said occlusal portion to said base portion, said connecting means including a connecting member having one of its ends rigidly connected to said occlusal portion, and its opposite end pivotally and loosely connected to said base portion to permit controlled limited movement of said occlusal portion relative to said base portion, said connecting member extending through said resilient intermediate portion, said intermediate portion being disposed generally half way between said occlusal surface and said ridge lap surface to provide upper and lower generally horizontally extending surfaces secured respectively to said occlusal portion and base portion, said occlusal portion and base portion and base portion providing respectively lower and upper surfaces contacting said intermediate portion surfaces, said lower and upper surfaces of said occlusal portion and base portion being generally congruently superposed with each other and with said intermediate portion surfaces, each said surface having an outer perimetral boundary, and said connecting member being disposed centrally within the boundaries of said surface, said connecting member being a U-shaped anchor wire, the base of which is rigidly secured to said occlusal portion to provide a pair of vertically extending legs, the distal ends of which are loosely pivotally secured to said base portion, said base portion being provided with vertically extending clearance holes through which said legs extend, said distal ends of said legs being turned at said ridge lap surface to prevent vertical movement of said legs away from said base portion.

3. An artificial tooth comprising a rigid base portion providing a ridge lap surface, a rigid occlusal portion providing an occlusal surface, a resilient intermediate portion sandwiched between and secured to said base portion and occlusal portion, and means for connecting said occlusal portion to said base portion, said connecting means including a pair of connecting members, each member having one of its ends rigidly connected to said occlusal portion, and its opposite end pivotally and loosely connected to said base portion to permit controlled limited movement of said occlusal portion relative to said base portion, said connecting members extending through said resilient intermediate portion, said connecting members being spaced apart in a central mesial-distal plane section of said tooth, said connecting members extending generally vertically between said occlusal portion and base portion, said basse portion providing vertically extending clearance holes extending vertically toward said ridge lap surface for receiving respectively said connecting members, said clearance holes being enlarged at their bases to provide sockets in said base portion, and said connecting members having enlarged ends trapped in said sockets.

4. An artificial tooth for use in a denture comprising a rigid base portion, a rigid occlusal portion, a resilient intermediate portion disposed between said base portion and said occlusal portion to permit said occlusal portion yieldably to move relative to said base portion, and means for connecting said occlusal portion to said base portion, said connecting means providing for limited movement of said occlusal portion relative to said base portion, said occlusal portion having a normal unloaded position relative to said base portion, said connecting means including a pair of anchor wires extending between said occlusal portion and said base portion, each of said wires being rigidly connected at one end to said occlusal portion and loosely pivotally connected at the other end to said base portion, said loose pivotal connections of said wires permitting said occlusal portion to move from its normal position toward said base portion to compress said intermediate portion and preventing movement of said occlusal portion from its normal position away from said base portion.

5. An artificial tooth for use in a denture comprising a base portion, an occlusal portion, and an intermediate portion sandwiched between and secured to said base portion and occlusal portion, said intermediate portion being resilient to permit said occlusal portion yieldably to move relative to said base portion, said occlusal portion providing, at its upper end, an occlusal surface and said base portion providing, at its lower end, a ridge lap surface, said intermediate portion being disposed generally at equal vertical distances from said occlusal surface and said ridge lap surface, said base portion being elongated in the mesialdistal direction, and a plurality of occlusal portions and intermediate portions are provided, each intermediate portion being sandwiched between one of said occlusal portions and said elongated base yieldably resiliently to support said one occlusal portion.

6. An artificial tooth for use in a denture comprising a base portion, an occlusal portion, and an intermediate portion sandwiched between and secured to said base portion and occlusal portion, said intermediate portion being resilient to permit said occlusal portion yieldably to move relative to said base portion, said occlusal portion providing, at its upper end, an occlusal surface and said base portion providing, at its lower end, a ridge lap surface, said intermediate portion being disposed generally at equal vertical distances from said occlusal surface and said ridge lap surface, said base portion and said occlusal portion providing respectively upper and lower generally horizontally extending bonding surfaces and said intermediate portion providing generally horizontally extending upper and lower surfaces bonded respectively to the lower and upper bonding surfaces of said occlusal portion and base portion, said bonding surfaces of said base portion and occlusal portion being provided with cavities therein for receiving the resilient material of said intermediate portion.

7. An artificial tooth for use in a denture comprising a rigid base portion, a rigid occlusal portion, a resilient intermediate portion disposed between said base portion and said occlusal portion to permit said occlusal portion yieldably to move relative to said base portion, and means for connecting said occlusal portion to said base portion, said connecting means including a pair of connecting members spaced apart in a central mesial-distal plane section of said tooth, each member having an upper end rigidly connected to said occlusal portion and a lower end pivotally and loosely connected to said base portion to permit controlled limited movement of said occlusal portion relative to said base portion.

8. The invention of claim 7 in which said occlusal portion has a normal unloaded position relative to said base portion, said connecting members being formed, at their lower ends, to engage said base portion to prevent movement of said occlusal portion from its normal position away from said base portion and to permit movement of said occlusal portion toward said base portion as resisted by said resilient portion.

* * * * *